US007915432B2

(12) United States Patent
Foster

(10) Patent No.: US 7,915,432 B2
(45) Date of Patent: Mar. 29, 2011

(54) METHOD FOR IMPROVING THE SHELF-LIFE OF HEMATOXYLIN STAINING SOLUTIONS

(75) Inventor: Patrick Foster, Wrentham, MA (US)

(73) Assignee: Cytyc Corporation, Marlborough, MA (US)

( * ) Notice: Subject to any disclaimer, the term of this patent is extended or adjusted under 35 U.S.C. 154(b) by 449 days.

(21) Appl. No.: 11/953,628

(22) Filed: Dec. 10, 2007

(65) Prior Publication Data

US 2008/0139827 A1 Jun. 12, 2008

Related U.S. Application Data

(60) Provisional application No. 60/874,407, filed on Dec. 12, 2006.

(51) Int. Cl.
*C07D 311/78* (2006.01)

(52) U.S. Cl. .................................................... 549/383

(58) Field of Classification Search ............. 549/383, 549/477; 435/40.5
See application file for complete search history.

(56) References Cited

FOREIGN PATENT DOCUMENTS

| JP | 59051279 | * | 3/1984 |
| JP | 09175960 | * | 7/1997 |

* cited by examiner

*Primary Examiner* — Taylor Victor Oh
*(74) Attorney, Agent, or Firm* — Theodore R. Allen

(57) ABSTRACT

A method is provided for improving the shelf-life of a nuclear staining solution. In particular, the present invention provides a method of adding an antioxidant to a hematoxylin staining solution which maintains the performance of the stain over its shelf-life.

5 Claims, 5 Drawing Sheets

METHOD FOR IMPROVING THE SHELF-LIFE OF HEMATOXYLIN STAINING SOLUTIONS

FIELD OF THE INVENTION

A method is provided for improving the shelf-life of a nuclear staining solution. In particular, the present invention provides a method of adding an antioxidant to a hematoxylin staining solution which maintains the performance of the stain over its shelf-life.

A BACKGROUND OF THE INVENTION

Cytology generally refers to the study of the structure, function and pathology of cells. In a clinical laboratory environment cytotechnologists and pathologists diagnose a patient's condition by visually examining specimens of the patient's cells. These cells are typically stained to better define the structure of the cells and to aid in the visual review of the cells.

One common cytological technique is a pap smear, in which the cells from a woman's cervix are sampled and analyzed in order to detect the presence of abnormal cells. The process involves collecting a specimen from a woman's cervix using a brush or related instruments, and the specimen is then transferred to a slide for subsequent processing. The slide containing the specimen is then stained using on or more staining solutions and the slides are then coverslipped. The slide can then be evaluated visually by a cytotechnologist or by an automated imaging system.

One of the commonly used stains for cytological analyses is the Hematoxylin stain. Hematoxylin, itself, is not a dye but is a natural compound extracted by boiling the wood of the South American and West Indian logwood tree (*Haematoxylon campechianum*), and partly purified by recrystallization. To become a dye, the hematoxylin first needs to be oxidized to form haematein, either through exposure to air and sunlight or UV light or by employing various agents such as including potassium permanganate, iodine, sodium iodate, sodium periodate, potassium periodate, hydrogen peroxide or mercuric oxide.

However, even at this stage except for a few applications, direct staining with haematein is usually unsuccessful and it is necessary to include various metallic salts, or mordants for the stain to work effectively. The combination of mordant and dye is known as a "lake" and in the case of haematein-mordant such lakes are often positively charged, behaving as cationic dyes at low pH. For the purposes of clarity and uniformity of terms, the haematein-mordant lake shall be referred to hereinafter as a hematoxylin stain or hematoxylin staining solution.

Hematoxylin stains bind to acidic components of a cell such as nuclear chromatin, mitotic spindles, fibrin, and other cellular components. The color of the stained structures depends on the various mordants used to make the hematoxylin stain. Potassium alum, the most common mordant, gives the stained structures a blue to purple color.

The present invention relates to a means for improving the shelf-life of a nuclear staining solution. In particular, the method of the present invention is related to adding an antioxidant to a hematoxylin staining solution which maintains the performance of the stain over its shelf-life.

SUMMARY OF THE INVENTION

Figure 1:
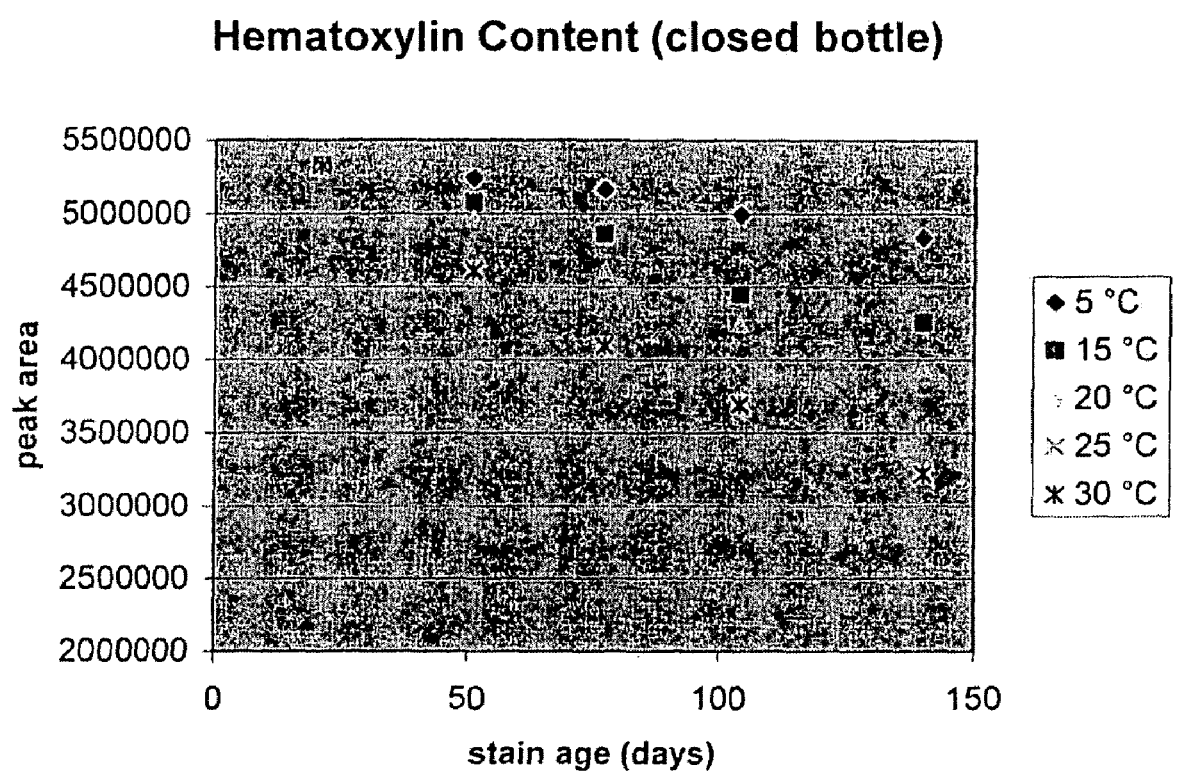
FIG. 1. is a graph of the content of hematoxylin versus stain age at various storage temperatures in a closed container.
Figure 2:
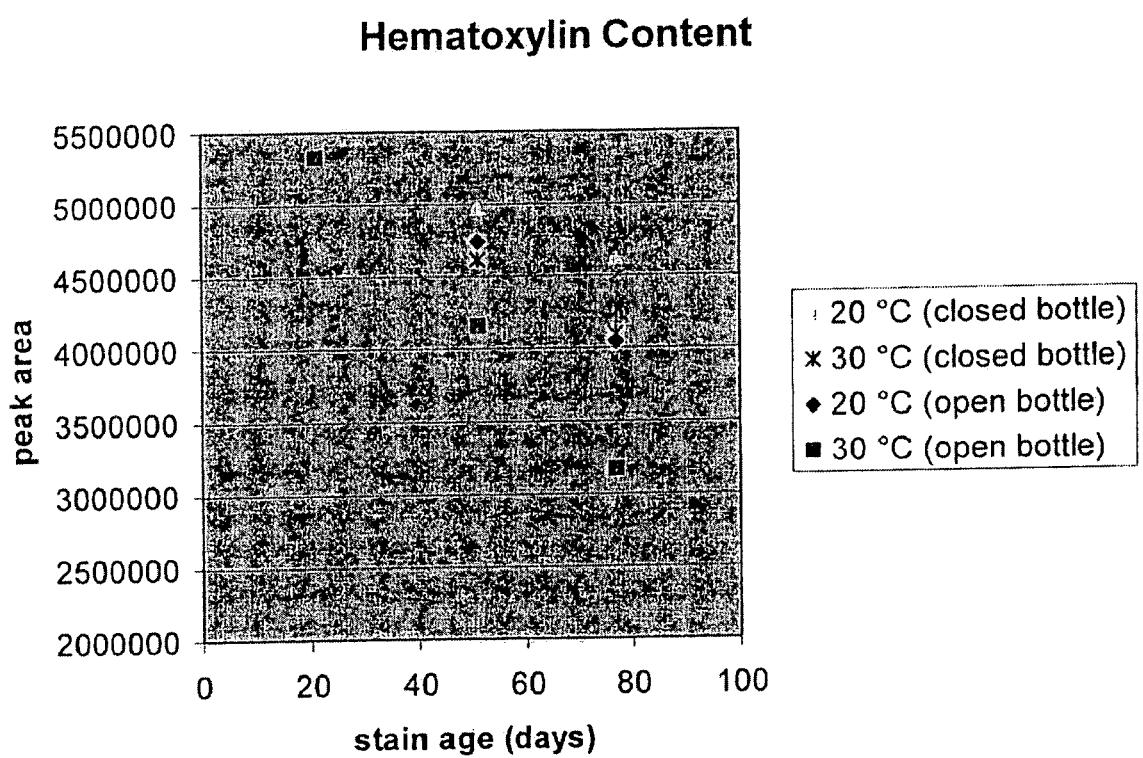
FIG. 2. is a graph of the content of hematoxylin versus stain age in a closed container as compared to an open container.
Figure 3:
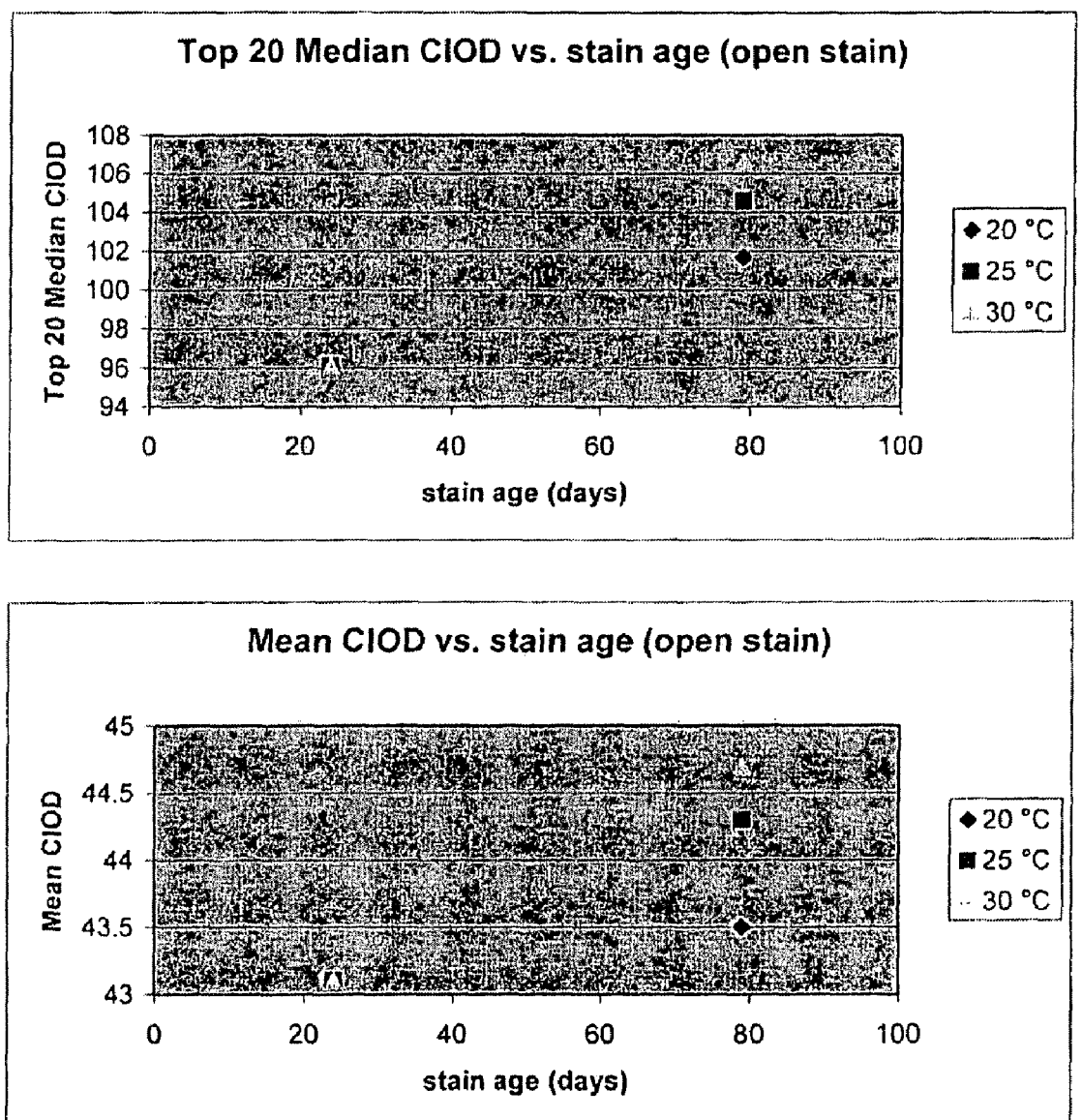
FIG. 3. is a graph of the relationship between storage temperature and non-specific staining.
Figure 4:
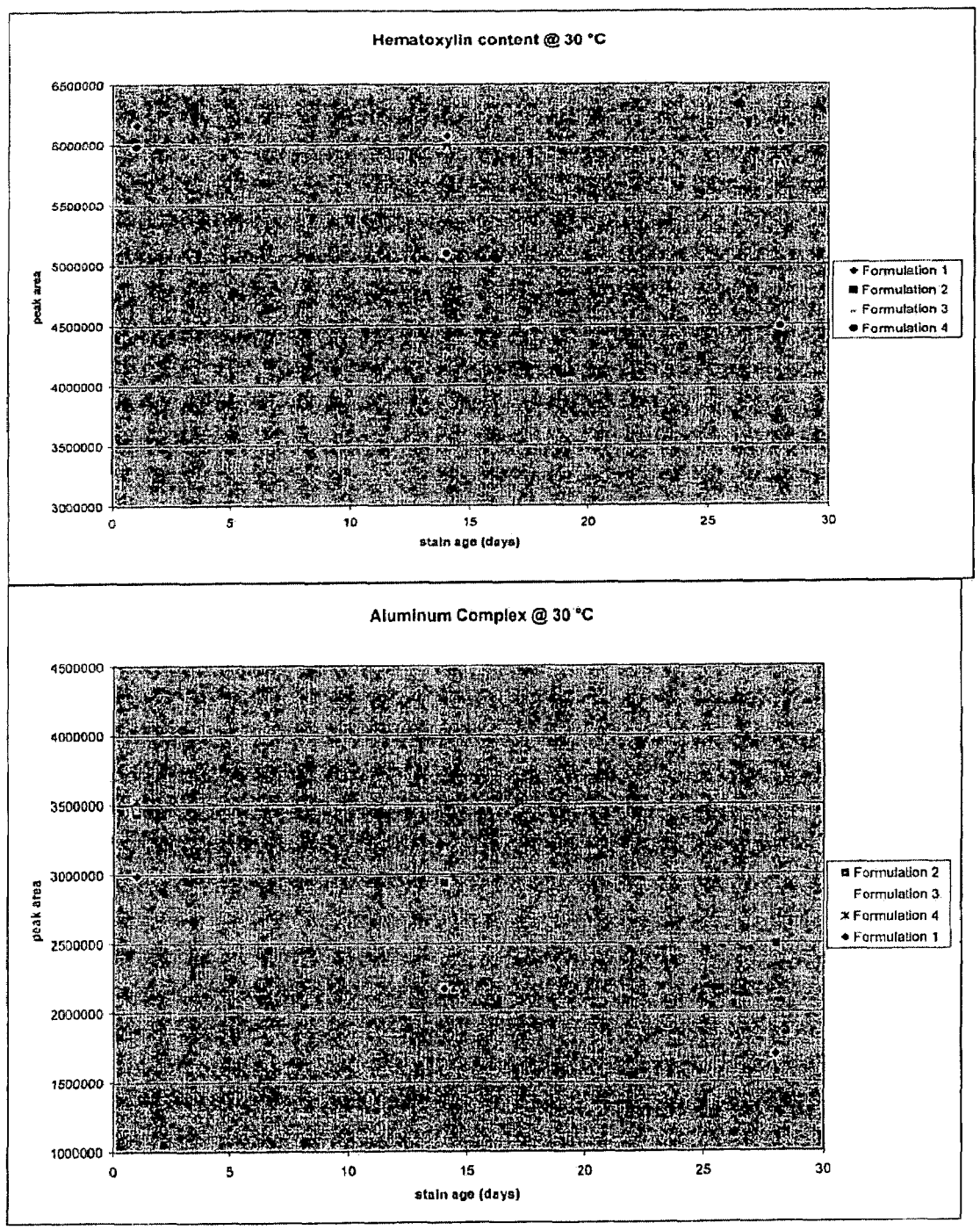
FIG. 4. is a graph of various formulations of a hematoxylin stain versus stain age.
Figure 5:
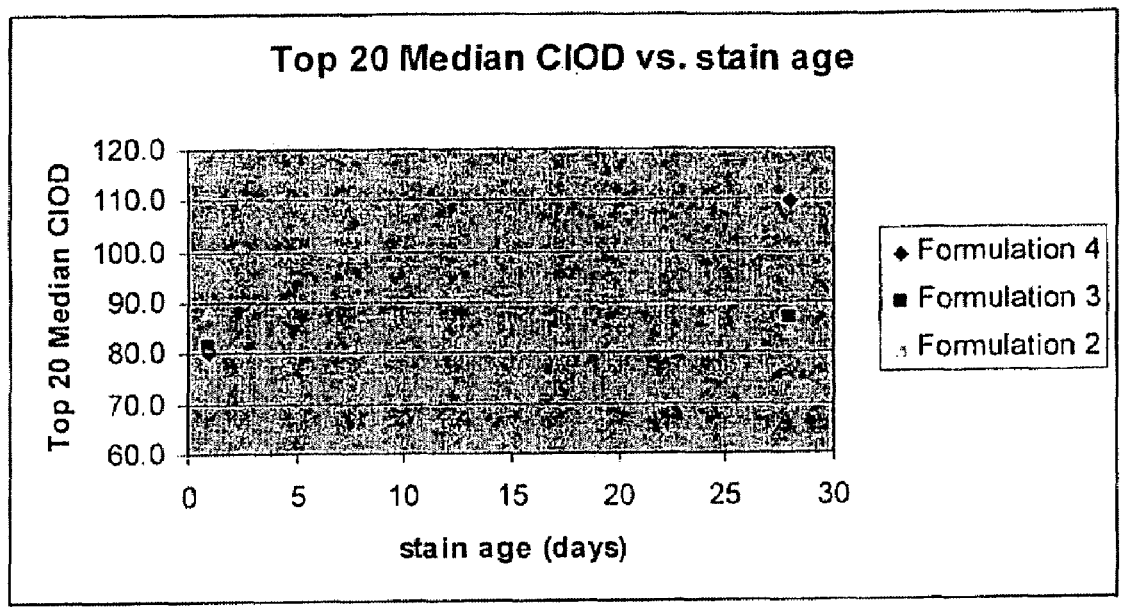
FIG. 5. is a graph of various formulations of a hematoxylin stain versus stain age.
Figure 5:
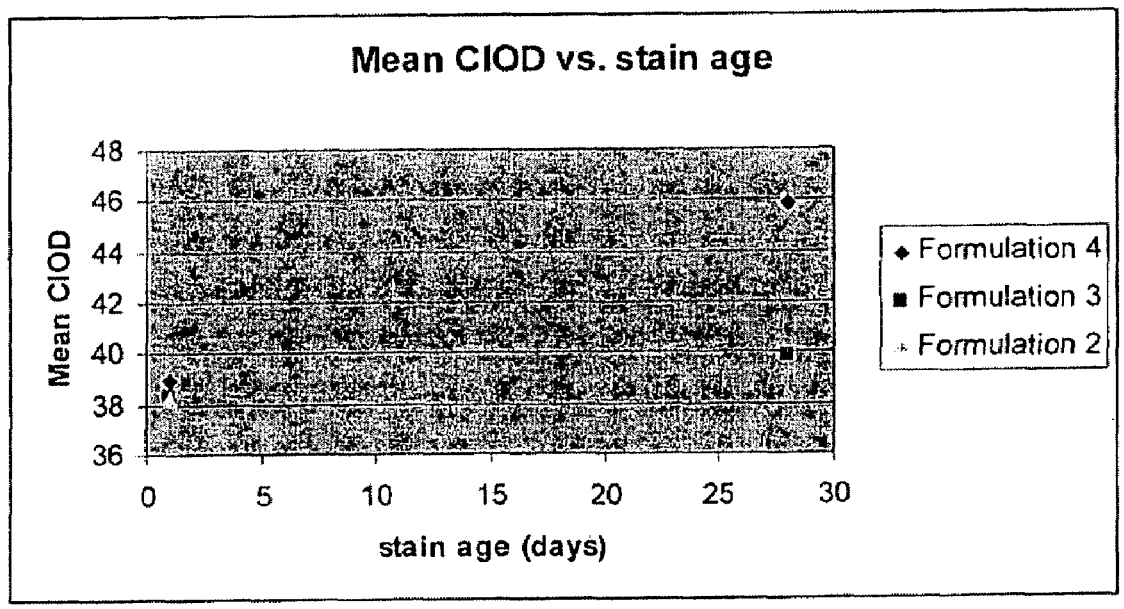

The present invention generally relates to a method for improving the shelf-life of a staining solution. In particular, the method of the present invention is related to adding an antioxidant to a nuclear staining solution which maintains the performance of the stain over its shelf-life.

In one aspect of the present invention, a method for reducing the oxidation of a nuclear stain comprising adding an antioxidant is presented. In one embodiment of the present invention, the nuclear stain is a hematoxylin stain. In another embodiment of the present invention, the antioxidant is selected from the group comprising Glutathione, Uric acid, Tannic acid, sodium bisulfite, butylated hydroxytoluene (BHT), butylated hydroxylanisole (BHA), propyl gallate (PG). In a preferred embodiment, the antioxidant is L-ascorbic acid.

In another aspect of the present invention, a method for increasing the shelf-life of a nuclear stain is presented. In one embodiment of the present invention, the shelf-life is increased from one to two, three, or more years. In another embodiment of the present invention, the shelf-life is increased by the addition of an antioxidant to the nuclear stain.

In yet another embodiment of the present invention, the nuclear stain is a hematoxylin stain. In still yet another embodiment of the present invention, the antioxidant is selected from the group comprising Glutathione, Uric acid, Tannic acid, sodium bisulfite, butylated hydroxytoluene (BHT), butylated hydroxylanisole (BHA), propyl gallate (PG). In a preferred embodiment, the antioxidant is L-ascorbic acid.

DETAILED DESCRIPTION OF THE INVENTION

Cytology is the branch of biology dealing with the study of the formation, structure, and function of cells. As applied in a laboratory setting, cytologists, cytotechnologists, and other medical professionals make medical diagnoses of a patient's condition based on visual examination of a specimen of the patient's cells. A typical cytological technique is a "Pap smear" test, in which cells are scraped from a woman's cervix and analyzed in order to detect the presence of abnormal cells, a precursor to the onset of cervical cancer.

Cell samples may be obtained from the patient by a variety of techniques including, for example, by scraping or swabbing an area, or by using a needle to aspirate body fluids from the chest cavity, bladder, spinal canal, or other appropriate area. The cell samples are placed in solution and subsequently collected and transferred to a glass slide for viewing under magnification. Fixative and staining solutions are typically applied to the cells on the glass slide, often called a cell smear, for facilitating examination and for preserving the specimen for archival purposes. The slides may then be evaluated visually by a cytotechnologist or by an automated imaging system. Cytological techniques are also used to detect abnormal cells and disease in other parts of the human body.

One prognostic indicator which has been valuable in the detection of abnormal cells in a Pap smear is DNA ploidy, which is the ratio of the quantity of DNA in a cancer cell to that in a normal cell in the resting phase of its growth cycle. In general, cells with normal resting-phase cellular DNA content (diploid) can be differentiated from those with abnormal DNA content (aneuploid). A cancer cell is aneuploid if it does not have the normal diploid number due to chromosome loss or an excess in chromosomes. "Hypoploidy" indicates loss of portions of or complete chromosomes. "Hyperploidy" or "hyperdiploidy" indicates that a cell contains more than the diploid number. Although standards vary, a chromosome number averaging at least 1.1 or 1.2 times the diploid number indicates hyperploidy or hyperdiploidy. These two latter terms partially overlap with the terms "tetraploidy" (twice the diploid number) and "hypertetraploidy" (more than twice the diploid number).

Various methods have been developed for measuring the DNA content of whole nuclei as a possible indicator of cancer including fluorescence in situ hybridization (FISH) [Marshall et al. (1996) Mutat. Res. 372:233-45; and Hande et al. (1997) Mutagenesis 12:125-31]; flow cytometry (FCM) [Stonesifer et al. (1987) Acta Cytol. 31:125-30; Remvikos et al. (1988) Int. J. Cancer 42:539-43; and Bronner et al. (1988) Am. J. Clin. Pathol. 89:764-9]; the Schutte method and the Hedley method [Tagawa et al. (1993) Cytometry 14:541-9]; Magnetic Resonance (MRI) [Takashima et al. (1996) Am. J. Roentgenol. 167:1297-304]; the stemline interpretation technique [Borchers et al. (1994) Urol. Int. 52:145-150]; and the analysis of spindle apparatus anomalies [Kochendorfer et al. (1996) Mutat. Res. 361:55-66].

Quantitative analysis, particularly the automated quantitative analysis of cytological, hematological and histological specimens requires exacting use of dyes, dye solutions and staining processes. Quantitative measurements used to differentiate normal from pathologic specimens may be expressed either as light transmission, integrated optical densities, ploidy, light scattering, light polarization effects and fluorescence. Since these measurements are strongly dependent on the stains and the staining process, the composition and performance of these stains must be tightly monitored and controlled.

There are numerous biological stains which can be used in conjunction with cytological or histological specimen preparations. Hematoxylin stain is a common type of nuclear stain used to assist in the visualization of biological material on a slide (see Biotech Histochem. 2005 March-April; 80(2):73-8). A hematoxylin stain is produced by the oxidation of hematoxylin to haematein using oxidizing agents such as sodium iodate or hydrogen peroxide. The haematein is then complexed to a transition metal (or mordant) such as iron or aluminum which results in a basic dye.

One drawback related to the use of hematoxylin stains is that the oxidation process takes place continuously throughout the life of the hematoxylin stain. As the free hematoxylin in solution is oxidized, the staining properties of the solution can change significantly. As the hematoxylin stain continues to age, the stain begins to exhibit more non-specific staining (i.e., increased cytoplasmic staining and non-DNA associated staining in the nuclei). Eventually, the stain becomes too oxidized and must be discarded. Thus, hematoxylin stains have a certain "shelf life". The shelf life of a stain can be considered as the length of time that the stain can function appropriately as a nuclear stain before it can no longer be considered suitable for its intended purpose. As such, a hematoxylin stain that has undergone a certain amount of oxidation may still be useful for cytological review of a specimen by a cytotechnologist, however, that same stain may not be satisfactory for automated quantitative analysis by a machine.

Automated quantitative analysis requires that a particular nuclear stain exhibit consistent staining performance. Commercial hematoxylin stains have a shelf-life of approximately one to three years depending upon the cytological application. For automated quantitative analysis, most hematoxylin stains will last for one year at room temperature although the shelf-life may be reduced by several factors including elevated temperatures and exposure to air. Thus, it would be advantageous to have a staining solution with a longer shelf life while maintaining its optimal staining characteristics even at higher temperatures and when exposed to air.

Numerous imaging systems make use of measures integrated optical density (IOD), to assist in the quantification of deoxyribonucleic acid (DNA) in a cell, such as the Automated Cellular Imaging System (ACIS) (ChromaVision, San Juan Capistrano, Calif.) and the ThinPrep® Imaging System (Cytyc Corporation, Marlborough, Mass.). The staining protocol for the ThinPrep® Imager has been designed to produce approximately stoichiometric nuclear staining. When nuclear staining is stoichiometric, the corrected integrated optical density (CIOD) is directly proportional to the amount of chromatin in the nucleus. The ThinPrep® Imager identifies artifacts and separates them from the objects being considered for ranking. The remaining objects are ranked on the basis of CIOD.

Mean CIOD is averaged over objects that have been classified by the Imager as intermediate cells. Since intermediate cells have high contrast between the nucleus and cytoplasm, the segmentation algorithm is relatively insensitive to subtle stain changes in intermediate cells. To determine stain uptake, intermediate cells are selected for calculating Mean CIOD; the high contrast seen with intermediate cells allows the segmentation algorithm to be more accurate. Therefore, since segmentation is accurate, Mean CIOD is a good measure of stain uptake.

Mean CV is a descriptor of An increase in CV can be an indicator that non-specific staining has increased. That is, a high CV can indicate that the nuclear stain is binding to additional sites (e.g. non-chromatin associated sites in the nucleus, and/or sites in the cytoplasm).

Top 20 Median CIOD is a measure of the median CIOD The cell types that fall into this area of the scatterplot tend to have thicker cytoplasms (e.g. squamous metaplastic cells) resulting in lower contrast between nucleus and cytoplasm than is typically seen for intermediate cells. If the Top 20 Median CIOD value is higher than the usual operating point, it may indicate poor contrast between the nucleus and cytoplasm which results in segmentation errors. If the Top 20 Median CIOD is lower than the usual operating point, it may indicate that the stain uptake in the nuclei is lower than optimal.

CIOD Ratio If the staining is stoichiometric, the ratio of Top 20 Median CIOD/Mean CIOD should be approximately equal to 2.

The method of the present invention relates to an improved staining solution to which an antioxidant has been added. The stain or staining solution of the present invention is comprised of a cytological or histological dye(s) capable of staining cellular material for further analysis by a technician or a professional. In one embodiment of the present invention the stain is a nuclear stain. In one preferred embodiment of the present invention the nuclear stain is hematoxylin, although other nuclear stains may be used such as Aniline Blue, Basic Fuchsin, Methylene Blue, Methyl Green, Safranin O, Carmine Alum, and Nuclear Fast Red (see Penny, D P et al, Analysis and testing of biological stains—The Biological Stain Commission Procedures. *Biotech. Histochem.*

77(5&6), 237-275, (2002). In another embodiment of the present invention, the hematoxylin stain is Gill Hematoxylin Stain; Harris Hematoxylin Stain; or Mayer's Hematoxylin Stain.

The addition of an antioxidant to a staining solution increases the shelf life of the staining solution. In one embodiment of the present invention, the antioxidant is added after the staining solution has undergone between 0%-90% oxidation. In another embodiment of the present invention, the antioxidant is added after the staining solution has undergone between 0%-50% oxidation.

In one embodiment of the present invention, the nuclear stain is a hematoxylin stain. In another embodiment of the present invention, the antioxidant is selected from the group comprising Glutathione, Uric acid, Tannic acid, sodium bisulfite, butylated hydroxytoluene (BHT), butylated hydroxylanisole (BHA), propyl gallate (PG). In a preferred embodiment, the antioxidant is L-ascorbic acid.

In another aspect of the present invention, a method for increasing the shelf-life of a nuclear stain is presented. In one embodiment of the present invention, the shelf-life is increased from one to two, three, or more years. In another embodiment of the present invention, the shelf-life is increased by the addition of an antioxidant to the nuclear stain. In yet another embodiment of the present invention, the nuclear stain is a hematoxylin stain. In still yet another embodiment of the present invention, the antioxidant is selected from the group comprising Glutathione, Uric acid, Tannic acid, sodium bisulfite, butylated hydroxytoluene (BHT), butylated hydroxylanisole (BHA), propyl gallate (PG). In a preferred embodiment, the antioxidant is L-ascorbic acid.

EXAMPLE 1

The graph in FIG. 1. illustrates the relationship between the storage temperature of a nuclear stain and the effectiveness of the stain. As the temperature increases, there is an increase in non-specific staining as demonstrated by the increase in the Top 20 Median CIOD measurements which is an indication of poor contrast between the staining of the nucleus versus the cytoplasm. Likewise, the increase in optical density measurement, as demonstrated by the increased Mean CIOD at elevated temperatures, can also be attributed to an increase in non-specific staining as the hematoxylin staining solution is oxidized.

In order to reduce the variability of the staining solution over its shelf life and to reduce the negative effects of temperature and air sensitivity, an antioxidant was added to the staining solution. Although numerous antioxidants would work equally as well, the antioxidant L-ascorbic acid was chosen as the primary antioxidant. Several different formulations of a hematoxylin staining solution were prepared. The formulations were prepared using the reagents shown in Table 1 below.

Clinical performance of the imager using slides that were stained at various nuclear stain ages can be tested by assessing abnormal specimen detection rates and percent agreement for abnormal specimens by comparing imager results to manual screening results.

This was tested on over 800 clinical specimens Using four different stain lots of approximate nuclear stain ages 0.5, 2, 6, or 12 months (lots D, A, B, C, respectively). Once clinical efficacy has been established, specification ranges for the imager derived parameters can be set such that any experimental condition that yielded results outside of the specifications would be considered to fail stain quality assessment. This method can be used to qualify new manufactured stain lots, new dye lots, changes in staining protocols, etc.

Automated Stain OC

If the above parameters are measured over a larger number of clinical cases, then the parameters tend to behave the same way as if they were measured over a very small set of pre-qualified specimens of specific specimen conditions. From Table 3 it can be seen that most of the measurements for nuclear stain lots A, B, and C fall within Mean±3 SD for "Mature" stain (Mean CV for lot C fall outside Mean±3 SD), and all measurements for nuclear stain lot D fall within Mean±3SD for "Young" stain. In this data set, the ratio of normal:abnormal specimens is approximately 2:1. Even with such a high proportion of abnormal specimens, the Top 20 Median CIOD which is only measured on normal cases for the experimental sets in Tables 1 and 2 falls within the Mean±3 SD range.

Since a 2:1 ratio of normal:abnormal represents a much higher proportion of abnormal specimens than would be expected in a usual clinical setting, it both Top 20 Median CIOD and CIOD Ratio will likely be useful in a clinical setting given a sufficient sample size. With a sufficient number of clinical specimens refined thresholds for each of the parameters can be set. Simple statistical methods such as a running average can be used to monitor stain quality. If the thresholds are exceeded, a slide event would be generated by the imager indicating a stain quality issue.

TABLE 2

Summary of Imager Derived parameters for 828 cases used to test Clinical performance.

| Stain Lot | Approx Nuclear Stain Age (mo) | Number of Specimens | Mean CIOD | Mean CV | Top 20 Median CIOD | CIOD Ratio |
|---|---|---|---|---|---|---|
| A | 2 | 198 | 42.8 | 10.7 | 92.0 | 2.1 |
| B | 6 | 208 | 43.6 | 9.8 | 97.7 | 2.2 |
| C | 12 | 202 | 43.3 | 12.4 | 115.4 | 2.7 |
| D | 0.5 | 220 | 41.0 | 10.8 | 89.3 | 2.2 |

TABLE 1

| Formulation | hematoxylin (grams) | sodium iodate (grams) | aluminum sulfate (grams) | water (grams) | ethylene glycol (grams) | acetic acid (grams) | ascorbic acid (grams) | ascorbic acid (eq) |
|---|---|---|---|---|---|---|---|---|
| 1 | 4.00 | 0.40 | 35.27 | 750 | 278 | 15 | 2.3 | 1 |
| 2 | 4.00 | 0.40 | 35.27 | 750 | 278 | 15 | 1.2 | 0.5 |
| 3 | 4.00 | 0.40 | 35.27 | 750 | 278 | 15 | 0.6 | 0.25 |
| 4 | 4.00 | 0.40 | 35.27 | 750 | 278 | 15 | 0 | 0 |

EQUIVALENTS

Those skilled in the art will recognize, or be able to ascertain using no more than routine experimentation, many equivalents to the specific embodiments of the invention described herein. The invention can be embodied in other specific forms without departing from the spirit or essential characteristics thereof. The present embodiments are therefore to be considered in all respects as illustrative and not restrictive. The scope of the invention is indicated by the appended claims, rather than by the foregoing description, and all changes which come within the meaning and range of equivalency of the claims are therefore intended to be embraced therein.

The invention claimed is:

1. A method for reducing the oxidation of a nuclear stain comprising adding an antioxidant sufficient to increase the shelf-life of the nuclear stain wherein the nuclear stain is hematoxylin and wherein the antioxidant is selected from the group consisting of glutathione, uric acid, tannic acid, sodium bisulfite, butylated hydroxytoluene, butylated hydroxylanisole, and propyl gallate.

2. The method of claim 1 wherein the antioxidant is L-ascorbic acid.

3. A method for reducing the oxidation of a hematoxylin stain comprising adding an amount of antioxidant sufficient to increase the shelf-life of the hematoxylin stain, wherein the antioxidant is selected from the group consisting of glutathione, uric acid, tannic acid, sodium bisulfite, butylated hydroxytoluene, butylated hydroxylanisole, and propyl gallate.

4. The method of claim 3 wherein the antioxidant is L-ascorbic acid.

5. A method for reducing the oxidation of a hematoxylin stain comprising adding an amount of L-ascorbic acid sufficient to increase the shelf-life of the hematoxylin stain.

* * * * *